United States Patent [19]

Shimomura

[11] Patent Number: 4,609,453

[45] Date of Patent: Sep. 2, 1986

[54] ENGINE AIR/FUEL RATIO SENSING DEVICE

[75] Inventor: Setsuhiro Shimomura, Himeji, Japan

[73] Assignee: Mitsubishi Denki Kabushiki Kaisha, Tokyo, Japan

[21] Appl. No.: 697,904

[22] Filed: Feb. 4, 1985

[30] Foreign Application Priority Data

Feb. 8, 1984 [JP] Japan .................................. 58-23223

[51] Int. Cl.⁴ ............................................. G01N 27/46
[52] U.S. Cl. .................................. 204/425; 204/1 T; 204/412; 204/426
[58] Field of Search ................. 204/1 S, 412, 421–429

[56] References Cited

U.S. PATENT DOCUMENTS

| | | | |
|---|---|---|---|
| 4,167,163 | 9/1979 | Moder | 204/424 |
| 4,272,329 | 6/1981 | Hetrick et al. | |
| 4,419,190 | 12/1983 | Dietz et al. | 204/1 S |
| 4,450,065 | 5/1984 | Yamada et al. | 204/426 |
| 4,472,262 | 9/1984 | Kondo et al. | 204/429 |
| 4,498,968 | 2/1985 | Yamada et al. | 204/426 |

*Primary Examiner*—T. Tung
*Attorney, Agent, or Firm*—Leydig, Voit & Mayer, Ltd.

[57] ABSTRACT

An engine air/fuel ratio sensing device for measuring the oxygen partial pressure or concentration in the exhaust gas of an engine. The device has a sensor and a control circuit coupled to each other. The sensor consists of an electrolyte oxygen pump cell and an electrolyte oxygen sensor cell, both cells having a gap portion therebetween. The control circuit provides a pumping current through a current limiting resistor to the pump cell and measures two terminal voltages across the current limiting resistor to derive the actual pump current and the internal resistance of the pump cell which are used to correct the actual pump current to a proper pump current dependent on the temperature to which the sensor is exposed, in accordance with a predetermined equation.

8 Claims, 6 Drawing Figures

FIG. 6

| Ip \ R | R1 | R2 | R3 | --- | Rn | Rn+1 | --- |
|---|---|---|---|---|---|---|---|
| Ip1 | Ipo1,1 | Ipo1,2 | Ipo1,3 | --- | Ipo1,n | Ipo1,n+1 | --- |
| Ip2 | Ipo2,1 | Ipo2,2 | Ipo2,3 | --- | Ipo2,n | Ipo2,n+1 | --- |
| Ip3 | Ipo3,1 | Ipo3,2 | Ipo3,3 | / | Ipo3,n | Ipo3,n+1 | / |
| --- | --- | --- | --- | / | --- | --- | / |
| Ipn | Ipon,1 | Ipon,2 | Ipon,3 | --- | Ipon,n | Ipon,n+1 | --- |
| Ipn+1 | Ipon+1,1 | Ipon+1,2 | Ipon+1,3 | / | Ipon+1,n | Ipon+1,n+1 | / |
| --- | --- | --- | --- | / | --- | --- | / |

ENGINE AIR/FUEL RATIO SENSING DEVICE

BACKGROUND OF THE INVENTION

This invention relates to a device for measuring an oxygen concentration within an exhaust gas from an internal combustion engine etc., to sense the air/fuel (hereinafter abbreviated as A/F) ratio and in particular to an improved engine A/F ratio sensing device of an oxygen pump type constructed using an ion conducting solid electrolyte.

It is hitherto well known in the art to control e.g. an engine of an automobile to run at a stoichiometric (theoretical) A/F ratio by sensing its combustion state in relation to the stoichiometric A/F ratio according to the variation of an electromotive force produced by the difference of the oxygen partial pressure between the exhaust gas and the atmosphere by means of an oxygen sensor constructed with an ion conducting solid electrolyte such as stabilized zirconia.

When the A/F ratio which is given by the weight ratio of air to fuel is the stoichiometric A/F ratio of 14.7, the above type oxygen sensor can provide a large output variation, while outside the stoichiometric A/F ratio it provides a substantially null output variation. Therefore, when the engine is operated at an A/F ratio outside the stoichiometric A/F ratio, the output of such an oxygen sensor can not be utilized.

Thus, an A/F ratio sensor of an oxygen pump type which eliminates such a disadvantage and enables the engine to be operated at any A/F ratio has already been proposed. However, such a sensor is not practical for the reason of an outstanding variation of its characteristic due to temperature variation.

FIG. 1 shows an arrangement of an A/F ratio sensing device of an oxygen pump type, and FIG. 2 shows a cross sectional view of the sensor in FIG. 1 taken along line II—II, which is disclosed in a related application Ser. No. 606,926 filed May 4, 1984.

In FIG. 1, within an exhaust pipe 1 of an engine (not shown) an A/F ratio sensor, generally designated by a reference numeral 2, is disposed. This sensor 2 is formed of a solid electrolyte oxygen pump cell 3, a solid electrolyte oxygen sensor cell 4, and a supporting base 5. The solid electrolyte oxygen pump cell 3 includes an ion conducting solid electrolyte (stabilized zirconia) 6 in the form of a plate with a thickness of about 0.5 mm having platinum electrodes 7 and 8 disposed on the respective sides thereof. The solid electrolyte oxygen sensor cell 4, similar to the pump cell 3, includes an ion conductive solid electrolyte 9 in the form of a plate having platinum electrodes 10 and 11 disposed on the respective sides thereof. The supporting base 5 supports the oxygen pump cell 3 and the oxygen sensor cell 4 so that they are oppositely disposed having a minute gap "d" of about 0.1 mm therebetween.

An electronic control unit 12 is electrically coupled to the pump cell 3 and the sensor cell 4. More specifically, the electrode 10 is connected through a resistor R1 to the inverting input of an operational amplifier A, the non-inverting input of which is grounded through a DC reference voltage source V. This DC reference voltage serves to control the output voltage of the sensor cell 4 to assume said voltage V according to the oxygen partial pressure difference between those within the gap and outside the gap. The electrode 7 is connected through a resistor Rs to the emitter of a transistor Tr whose collector is grounded through a DC power source B and whose base is connected to the output of the operational amplifier A and the inverting input of the operational amplifier A through a capacitor C. The electrodes 8 and 11 are grounded.

U.S. Pat. No. 4,272,329 discloses the principle of an A/F ratio sensing device of an oxygen type.

In operation, when the oxygen partial pressure within the gap portion between the cells 3 and 4 is the same as the oxygen partial pressure outside the gap portion, the sensor cell 4 generates no electromotive force. Therefore, the inverting input of the operational amplifier A receives no voltage and, accordingly the operational amplifier A provides as an output therefrom a maximum voltage corresponding to the reference voltage V to the base of the transistor Tr. Therefore, the transistor Tr is made conductive to cause a pump current Ip to flow through the electrodes 7 and 8 of the pump cell 3 from the voltage source B. Then the pump cell 3 pumps oxygen present in the gap portion "d" into the exhaust pipe 1. As a result, the sensor cell 4 develops an electromotive force "e" thereacross according to the oxygen partial pressure difference on both sides of the cell 4.

Therefore, the oxygen sensor cell 4 applies the electromotive force "e" generated across the electrodes 10 and 11 to the inverting input of the operational amplifier A through the resistor R1. The operational amplifier A provides an output now proportional to the difference between the electromotive force "e" and the reference DC voltage V applied to the non-inverting input. The output of the operational amplifier A drives the transistor Tr to control the pump current Ip.

Thus, the electromotive force "e" approaches the reference voltage V. Accordingly, the control unit 12 reaches an equilibrium state and serves to provide a pump current Ip necessary for keeping the electromotive force "e" at the predetermined reference voltage V. The resistor Rs serves to provide an output corresponding to the pump current Ip supplied from the DC power source B as a pump current supply means. The pump current Ip corresponds to an A/F ratio value. This pump current Ip is converted into a voltage by the resistor Rs and is sent to a fuel control unit (not shown) so that the fuel control unit may be controlled at a desired A/F ratio. The resistance of the resistor Rs is selected so as to prevent the pump current Ip from flowing excessively from the DC power source B. The capacitor C forms an integrator associated with the operational amplifier A and serves to make the electromotive force "e" precisely coincident with the reference voltage V.

One example of the static characteristics of an A/F ratio sensing device of an oxygen pump type thus constructed in the form of a negative feedback control is shown in FIG. 3. A solid line indicates a characteristic of pump current Ip as a function of A/F ratio when the A/F ratio sensor 2 is exposed at 600° C. while a dotted line indicates a characteristic at 800° C. It is found that such a characteristic variation gives rise to the thermal variation of the ion conductivity of the ion conducting solid electrolytes 6 and 9, respectively forming the solid electrolyte oxygen pump cell 3 and the solid electrolyte oxygen sensor cell 4. Experiments reveal that as the temperature of the A/F ratio sensor is varied over a temperature range of an engine exhaust gas, the current Ip, flowing through the oxygen pump cell 3, corresponding to the same A/F ratio varies up to several ten percentages thereof, resulting in an unpractical A/F ratio sensor.

On the other hand, FIG. 4 shows a temperature dependency of the electrical resistance of the ion conducting solid electrolytes 6 and 9. Since this characteristic is common to various solid electrolytes, the application of this characteristic shown in FIG. 4 enables the temperature variation of the A/F ratio sensor to be corrected.

SUMMARY OF THE INVENTION

It is accordingly an object of the invention to provide an A/F ratio sensing device of an oxygen pump type, free from such a thermal characteristic variation as above noted, by the detection of the thermal characteristic variation the A/F ratio sensor per se from the variation of its internal resistance and by the correction of same.

In order to accomplish this object, the present invention provides an air/fuel ratio sensing device for an engine comprising an air/fuel sensor means having a gap portion for introducing an exhaust gas of the engine, a solid electrolyte oxygen pump cell for controlling an oxygen partial pressure within the gap portion, and a solid electrolyte oxygen sensor cell for producing an electromotive force corresponding to the difference between the oxygen partial pressure in the exhaust gas within the gap portion and the oxygen partial pressure in the exhaust gas outside the gap portion; and a control circuit means, coupled to the sensor means, having a current amplifier means for supplying to the oxygen pump cell a pump current necessary for keeping the oxygen partial pressure at a predetermined value, and a resistor inserted in the electrical path through which the pump current flows for limiting the pump current to a predetermined value, the control circuit means further comprising: a voltage measuring means, connected to the resistor, for measuring and providing as outputs therefrom the terminal voltage across the resistor and the terminal voltage across the oxygen pump cell, a computing means, connected to the voltage measuring means, for calculating from the terminal voltage across the resistor and the resistance of the resistor a first value corresponding to the pump current and for calculating from the first value and the terminal voltage across the oxygen pump cell a second value corresponding to the internal resistance of the oxygen pump cell, and a calibrating means, connected to the computing means, for providing as an air/fuel signal therefrom a third value obtained by calibrating the first value in accordance with a predetermined relationship including the first value and the second value as a parameter.

The calibrating means preferably comprises a storage means for storing a plurality of typical values representative of the first and second values as well as numerical values respectively corresponding to the combinations of the first and second values, and a computing means for searching four of the numerical values respectively corresponding to the combinations of respective two typical values sandwiching the respective values of the first and second values and for calculating a numerical value, as the third value, corresponding to the combination of the first and second values by means of an interpolating operation from the four numerical values.

The calibrating means calculates the third value (Ipo) from a calibrating equation $Ipo = Ip(1 + J \times \ln R/Ro)^C$ by using the first value (Ip) and second value (R), Ro, J, and C being constants. Also, the calibrating means calculates the third value (Ipo) from a calibrating equation $Ipo = Ip\{1 + CJ \times \ln(R - Ro)/Ro\}$ by using the first value (Ip) and second value (R), Ro, J, and C being constants. The constant C is preferably in the range of about 0.75–1.0.

BRIEF DESCRIPTION OF THE DRAWINGS

Throughout the figures, the same reference numerals indicate identical or corresponding portions.

DETAILED DESCRIPTION OF THE PREFERRED EMBODIMENT

One preferred embodiment of an A/F ratio sensing device of an oxygen pump type for an engine in accordance with the present invention will now be described in detail with reference to the accompanying drawings, particularly FIGS. 5 and 6.

Figure 1:
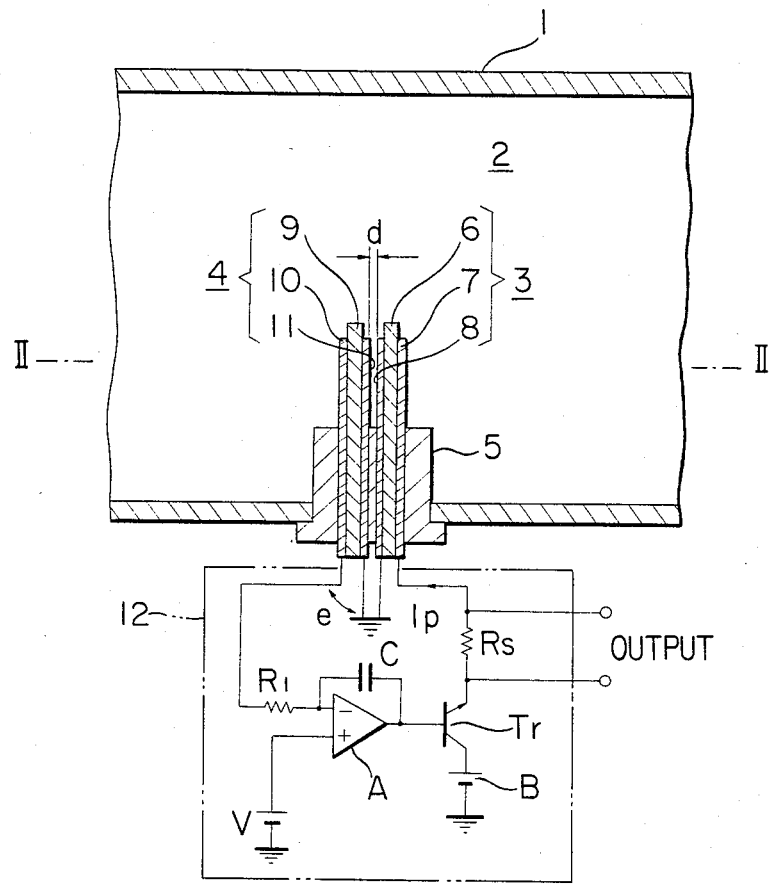
FIG. 1 shows an arrangement of an A/F ratio sensing device of an oxygen pump type described in a related application Ser. No. 606,926.
Figure 2:
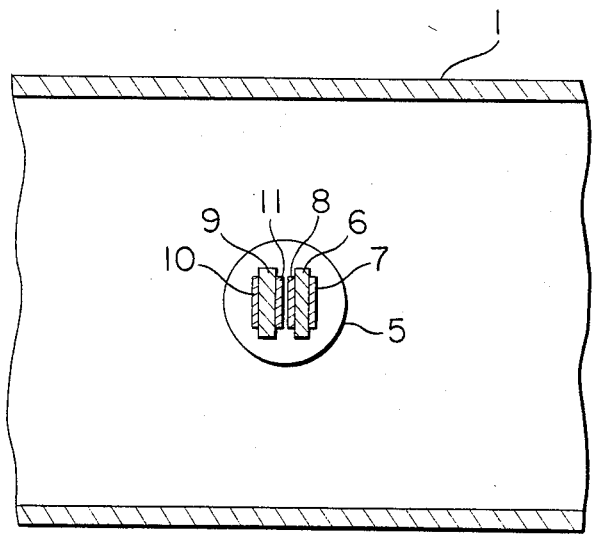
FIG. 2 shows a cross-sectional view of the sensor in FIG. 1, taken along line II—II.
Figure 3:
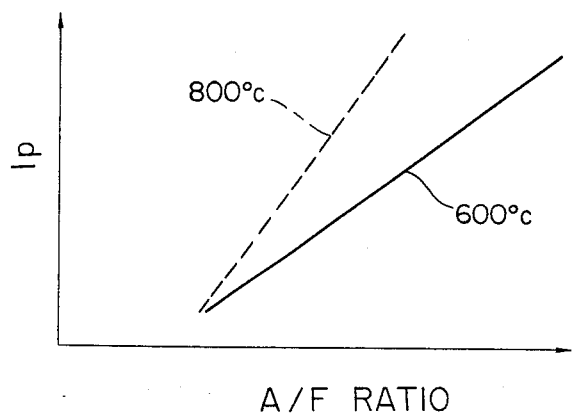
FIG. 3 shows characteristic curves of the sensing device in FIG. 1 wherein the ordinate axis denotes a pump current Ip and the abscissa axis denotes an A/F ratio.
Figure 4:
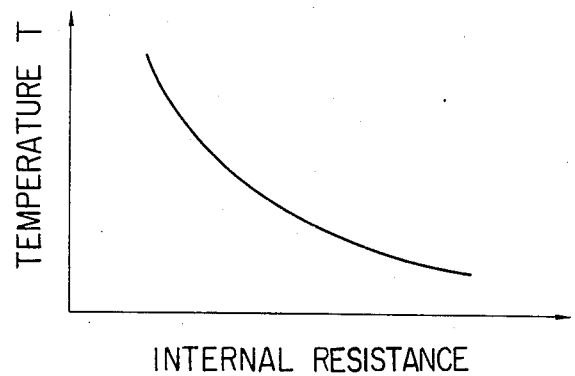
FIG. 4 shows characteristic curves of the sensing device in FIG. 1 wherein the ordinate axis denotes temperature T and the abscissa axis denotes an internal resistance R.
Figure 5:
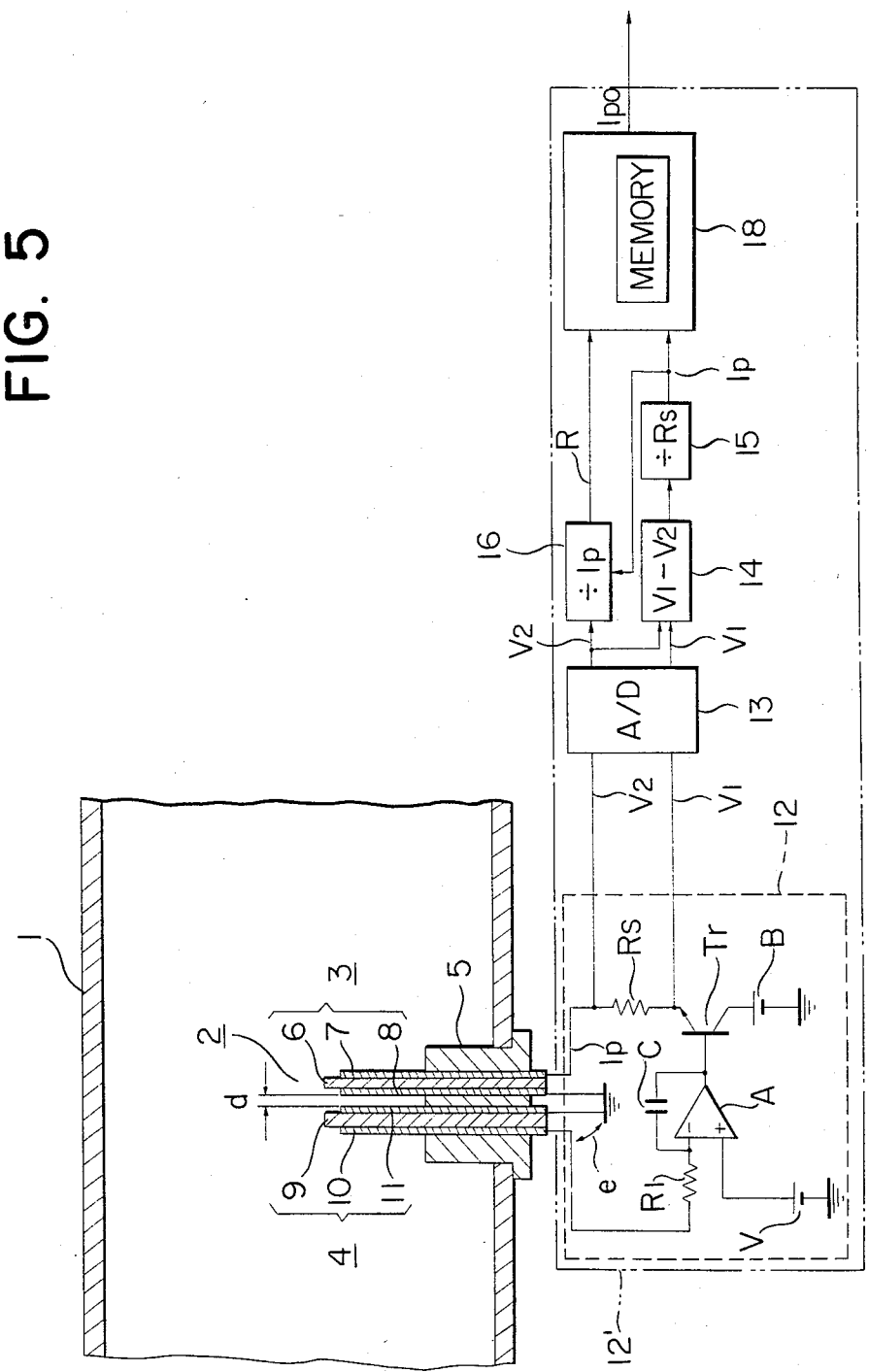
FIG. 5 shows an arrangement of an A/F ratio sensing device of an oxygen pump type, associated with an exhaust pipe, in accordance with one embodiment of the present invention; and, FIG. 6 shows a data map used in the present invention.

In FIG. 5, the difference between the arrangement of this invention and that of FIG. 1 is the provision of a control unit 12'. More specifically, this control unit 12', in addition to the control unit 12 having the same arrangement as that shown in FIG. 1, includes an A/D converter 13 of a two channel type, and computing portions 14–18. The two inputs of the A/D converter 13 are connected across the resistor Rs. The input of the computing portion 14 is connected to one output of the A/D converter 13 to calculate a terminal voltage v1-v2 across the resistor Rs. The input of the computing portion 15 is connected to the output of the computing portion 14 to calculate the pump current Ip by dividing v1-v2 by the resistance Rs. The one input of the computing portion 16 is connected to the other output of the A/D converter 13 and the other input of same is connected to the output of the computing portion 15 to calculate the internal resistance R of the oxygen pump cell 3 by dividing the terminal voltage v2 across the oxygen pump cell 3 by the pump current Ip. The two inputs of the computing portion 18 are respectively connected to the outputs of the computing portions 15 and 16 to calculate a proper pump current Ipo by correcting the pump current Ip with respect to the internal resistance R.

In the arrangement of FIG. 5, the terminal voltages v1 and v2 of the resistor Rs are given by the following equations:

$$v1 = Ip(Rs + R) \quad (1)$$

$$v2 = IpR \quad (2)$$

The terminal voltages v1 and v2 are respectively converted into digital signals by the A/D converter 13 for the facilitation of the computation processes, and the digitalized terminal voltages v1 and v2 are provided for the computing portion 14 which calculates the difference between the terminal voltages v1 and v2. This difference is divided by the resistance Rs in the computing portion 15 whose output therefore assumes $(v1-v2)/Rs = \{Ip(Rs+R) - IpR\}/Rs = Ip$ from equations (1) and (2), resulting in the calculation of the pump current Ip. In the computing portion 16, the terminal voltage v2 is divided by the output of the computing portion 15, i.e., Ip. Therefore, the output of the computing portion 16 assumes $v2/Ip = IpR/Ip = R$ from equation (2), resulting in the calculation of the internal resistance R of the oxygen pump cell 3. This internal resistance R together with the pump current Ip are inputed to the computing portion 18 in which the pump current Ip is corrected, i.e., calibrated to the pump current Ipo in a reference temperature To. The calibration is made on the basis of the relationship as described hereinbelow.

When the pump current Ip is controlled so as to keep the electromotive force "e" of the oxygen sensor cell 10 at a constant value, the relationships $$e = (RT/4F)\ln(Pa/Pv) \tag{3}$$

$$Ip = (4eDA/KTL)(Pa - Pv) \tag{4}$$

are established. Equation (3) is the famous Nernst's equation wherein Pa and Pv respectively designate oxygen partial pressures inside and outside the gap "d" as parameters representative of A/F ratio. It is to be noted that R designates the gas constant, F the Faraday's constant, and T temperature. Equation (4) indicates a relationship given at the time when a rate of oxygen pumped out of the gap "d" by the pump current Ip equilibrates with a rate of oxygen flown in the gap "d" by diffusion, in which e designates the electric charge of electron, D the diffusion coefficient, A the cross sectional area of the opening of the gap "d", K the Boltzmann's constant, and L the effective diffusion path length. From equations (3) and (4), we obtain $$Ip = (4eDA/KTL)Pa \tag{5}$$

On the other hand, it is known that the diffusion coefficient D of gas is proportional to the 1.75th power of temperature. Therefore, assuming the proportion constant be G, $D = GT^{1.75}$ is given. By substituting this in equation (5), we obtain $$Ip = (4eGA/KL)T^{0.75} \times Pa \tag{6}$$

Namely, it is found that the pump current Ip is proportional to the oxygen partial pressure Pa, i.e., A/F ratio and the 0.75th power of temperature T. In equation (6), assuming the pump current at the reference temperature To be Ipo, we obtain $$Ipo = (4eGA/KL)To^{0.75} \times Pa \tag{7}$$

From equations (6) and (7), we obtain $$Ipo = Ip(To/T)^{0.75} \tag{8}$$

Equation (8) indicates that the pump current Ip at an arbitrary temperature T can be calibrated to the pump current Ipo at the reference temperature To. It is to be noted that various experiments show that since equation (8) can not realize a precise calibration due to some effect caused by the structure of the sensor as well as temperature ununiformity and so on, it is desirable to express $$Ipo = Ip(To/T)^C \tag{9}$$

and to determine the exponent C based on practically measured data. Also in the arrangement of FIG. 5, it has been found according to experiments that C is preferably in the order of 0.75–1.0.

On the other hand, it is known that the relationship between the internal resistance R of the solid electrolyte and temperature T is given by $$To/T = 1 + (To/B) \times \ln R/Ro \tag{10}$$

It is to be noted that Ro designates a resistance which the solid electrolyte exhibits at the reference temperature To and B is a constant. By substituting equation (10) in equation (9), we get $$Ipo = Ip(1 + J \times \ln R/Ro)^C \tag{11}$$

where J = To/B. Hence, the computing portion 18 performs the calculation of equation (11) by using the pump current Ip which is the output of the computing portion 15 and the resistance R which is the output of the computing portion 16, thereby determining the pump current Ipo at the reference temperature To.

It is to be noted that if a micro-processor which is hard to perform a logarithm calculation or an exponential calculation is used as the computing portion 18, the pump current Ipo at the reference temperature To may be simply determined by the following equation $$Ipo = Ip\{1 + CJ(R - Ro)/Ro\} \tag{12}$$

which is a first order equation approximated instead of equation (11).

Also, an interpolating calculation may be made in the computing portion 18 by using map data shown in FIG. 6 and stored in a memory in the computing portion 18. The abscissa of the map data denotes typical points R1, R2, R3, —, Rn, Rn+1, —of the resistance R and the ordinate denotes typical points Ip1, Ip2, Ip3, —, Ipn, Ipn+1, —of the pump current Ip. Each of the cross points of the typical points on the abscissa and the ordinate indicates the pump current Ipo calibrated corresponding to the reference resistance Ro, i.e., the reference temperature To.

In this map data, for example, should the current Ip determined in the computing portion 15 be equal to Ip3 and the resistance R determined in the computing portion 16 be equal to R3, the value Ipon,3 stored in the memory in the computing portion 18 is outputed as the current Ipo.

Further, for example, should the current Ip determined in the computing portion 15 be a value which is between the tabulated values Ipn and Ipn+1, and the resistance R determined in the computing portion 16 be a value which is between the tabulated values Rn and Rn+1, an interpolating step is performed in the portion 18 according to conventional methods. Namely, from the combinations of typical point Rn which is smaller than and closest to the resistance R and of the typical points Ipn and Ipn+1 sandwiching the pump current Ip (i.e., the tabulated values closest to the current Ip), two calibrated pump currents(Ipon,n) and (Ipon+1,n) are retrieved by the operation of the computing portion 18. From the combination of the retrieved values (Ipn,Ipon,n) and (Ipn+1, Ipon+1,n), a pump current (Ipo,n) is determined by the interpolating operation due to the fact that the pump current Ip is intermediate between Ipn and Ipn+1. The process of the interpolating operation is well known so that the description thereof is omitted.

Then, from the combinations of typical point Rn+1 which is larger than and closest to the resistance R and of the typical points Ipn and Ipn+1 sandwiching the pump current Ip, two calibrated pump currents (Ipon,n+1) and (Ipon+1,n+1) are retrieved by the operation of the computing portion 18. From the combination of the retrieved values (Ipn, Ipon,n+1) and (Ipn+1, Ipon+1,n+1), a pump current (Ipo,n+1) is determined by the interpolating operation due to the fact that the pump current Ip is intermediate between Ipn and Ipn+1. Then, from the combinations of typical point Rn+1 which is larger than and closest to the resistance R and of the typical points Ipn and Ipn+1 sandwiching the pump current Ip, two calibrated pump currents (Ipon,n+1) and (Ipon+1,n+1) are retrieved by the operation of the computing portion 18. From the combination of the retrieved values (Ipn, Ipon,n+1) and (Ipn+1, Ipon+1,n+1), a pump current (Ipo,n+1) is determined by the interpolating operation due to the fact that the pump current Ip is intermediate between Ipn and Ipn+1.

Next, from the combination (Rn, Ipo,n) of the above determined pump current (Ipo,n) corresponding to the resistance Rn and the combination (Rn+1, Ipo,n+1) of the pump current (Ipo,n+1) corresponding to the resistance Rn+1, the pump current Ipo is calibrated corresponding to the resistance R by the interpolating operation. It is to be noted that this calibrated pump current Ipo has a value calibrated at the reference temperature To for the pump current Ip, as above described.

The pump current Ipo thus calibrated is used as a signal representative of an A/F ratio whereby the A/F ratio sensing device of an oxygen pump type according to this invention can be disposed in the exhaust gas path which is not constant in temperature.

As mentioned above, according to the A/F ratio sensing device of this invention, the following excellent advantages are effected:

(1) since the pump current representative of an A/F ratio is calibrated on the basis of the temperature of the A/F ratio sensor, a precise A/F ratio signal having eliminated therefrom characteristic variation due to thermal variation may be always obtained;

(2) since the temperature of the sensor is represented by the internal resistance of the oxygen pump cell forming the sensor, no particular thermal sensor is needed;

(3) the internal resistance of the oxygen pump cell can be easily calculated by measuring a terminal voltage across a resistor through which the pump current of the oxygen pump cell flows.

Consequently, an engine can be operated at any A/F ratio irrespective of temperature variation.

It is to be noted that while this invention has been described along the above embodiment, it should not be limited to the shown and described embodiment but various modifications may be made by any one of ordinary skills in the art without departing from the spirit of this invention.

What I claim as a patent is:

1. An air/fuel ratio sensing device for an engine comprising an air/fuel sensor means having a gap portion for introducing an exhaust gas of said engine, a solid electrolyte oxygen pump cell for controlling an oxygen partial pressure within said gap portion, and a solid electrolyte oxygen sensor cell for producing an electromotive force corresponding to the difference between the oxygen partial pressure in the exhaust gas within said gap portion and the oxygen partial pressure in the exhaust gas outside said gap portion; and a control circuit means, coupled to said sensor means, having a current amplifier means for supplying to said oxygen pump cell a pump current necessary for keeping said oxygen partial pressure at a predetermined value, and a resistor (Rs) inserted in the electrical path through which said pump current flows for limiting said pump current to a predetermined value, said control circuit means further comprising:

a voltage measuring means, connected to said resistor, for measuring and providing as outputs therefrom the terminal voltage across said resistor and the terminal voltage across said oxygen pump cell, a computing means, connected to said voltage measuring means, for calculating from said terminal voltage across said resistor and the resistance of said resistor a first value (Ip) corresponding to said pump current and for calculating from said first value and the terminal voltage across said oxygen pump cell a second value (R) corresponding to the internal resistance of said oxygen pump cell, and a calibrating means, connected to said computing means, for providing as an air/fuel signal therefrom a third value (Ipo) obtained by calibrating said first value in accordance with a predetermined relationship including said first value and said second value as a parameter.

2. An air/fuel ratio sensing device for an engine as claimed in claim 1 wherein said calibrating means comprises a storage means for storing a plurality of typical values representative of said first and second values as well as numerical values respectively corresponding to the combinations of said first and second values, and a computing means for searching four of said numerical values respectively corresponding to the combinations of respective two typical values sandwiching the respective values of said first and second values and for calculating a numerical value, as said third value, corresponding to the combination of said first and second values by means of an interpolating operation from said four numerical values.

3. An air/fuel ratio sensing device for an engine as claimed in claim 2 wherein said calibrating means determines said third value (Ipo) from the calibrating equation $Ipo = Ip(1 + J \times \ln R/Ro)^C$ by using said first value (Ip) and second value (R), said Ro, J, and C being constants.

4. An air/fuel ratio sensing device for an engine as claimed in claim 3 wherein said constant C is in the range of about 0.75–1.0.

5. An air/fuel ratio sensing device for an engine as claimed in claim 2 wherein said calibrating means determines said third value (Ipo) by executing the calibrating equation $Ipo = Ip\{1 + CJ \times \ln(R \times Ro)/Ro\}$ by using said first value (Ip) and second value (R), said Ro, J, and C being constants.

6. An air/fuel ratio sensing device for an engine as claimed in claim 5 wherein said constant C is in the range of about 0.75–1.0.

7. An air/fuel ratio sensing device for an engine as claimed in claim 1 wherein said calibrating means determines said third value (Ipo) from the calibrating equation $Ipo = Ip(1 + J \times \ln R/Ro)^C$ by using said first value (Ip) and second value (R), said Ro, J, and C being constants.

8. An air/fuel ratio sensing device for an engine as claimed in claim 1 wherein said calibrating means determines said third value (Ipo) by executing the calibrating equation $Ipo = Ip\{1 + CJ \times \ln(R - Ro)/Ro\}$ by using said first value (Ip) and second value (R), said Ro, J, and C being constants.

* * * * *